US00PP09987P

United States Patent [19]

Kawamoto

[11] Patent Number: Plant 9,987

[45] Date of Patent: Aug. 5, 1997

[54] HYBRID TEA ROSE PLANT NAMED 'KAWAMOBLUE'

[75] Inventor: Hiromoto Kawamoto, Gifu-Ken, Japan

[73] Assignee: Carlton Rose Nurseries, Inc., Portland, Oreg.

[21] Appl. No.: 587,764

[22] Filed: Dec. 15, 1995

[51] Int. Cl.[6] ..... A01H 5/00

[52] U.S. Cl. ..... Plt./11

[58] Field of Search ..... Plt./11, 18, 19

[56] References Cited

U.S. PATENT DOCUMENTS

P.P. 5,858 1/1987 Weeks ..... Plt./11

P.P. 6,812 5/1989 Christensen ..... Plt./11

*Primary Examiner*—Howard J. Locker

*Attorney, Agent, or Firm*—Chernoff, Vilhauer, McClung & Stenzel

[57] ABSTRACT

A vigorous rose plant of the Hybrid Tea class obtained as a seedling from an unnamed seed parent and a pollen parent named 'Blue Moon' provides abundant long-lasting purple flowers which substantially maintain their true color on a continuous basis when grown in a greenhouse.

1 Drawing Sheet

BACKGROUND AND SUMMARY OF THE INVENTION

The present invention relates to a new and distinct variety of Hybrid Tea rose plant, a seedling resulting from a definite effort to produce an improvement of this class of rose. The object of the present invention is to provide a rose plant of the Hybrid Tea class which is capable of producing quality-cut flowers under greenhouse conditions.

The primary features of this new variety which connotates its distinctive advantage over previously existing types is its ability to produce flowers having a striking purple color from a plant which will continuously yield cut flowers under greenhouse conditions. It differs from its parents by having a deeper purple color flower and its ability to produce five to ten more blooms per year when grown in a greenhouse.

The variety of rose plant of the present invention was obtained at Gifu-Ken, Japan as a seedling from an unnamed seed parent and a pollen parent named 'Blue Moon.' The crossing was made in March 1987, the first seed of the crossing was sown in December 1987 and the first flower appeared from these seedlings in May 1988.

Asexual reproduction of this new variety in Wasco, Calif., by means of budding, shows that its unique characteristics come true to form and are established and transmitted through succeeding propagations.

BRIEF DESCRIPTION OF THE DRAWINGS

In the accompanying drawings typical specimens of vegetative growth and flowers of the new variety are shown in different stages of development and are depicted in color as nearly true as is reasonably possible to make in color illustrations of this character.

DETAILED DESCRIPTION OF THE DISCLOSURE

Figure 1:
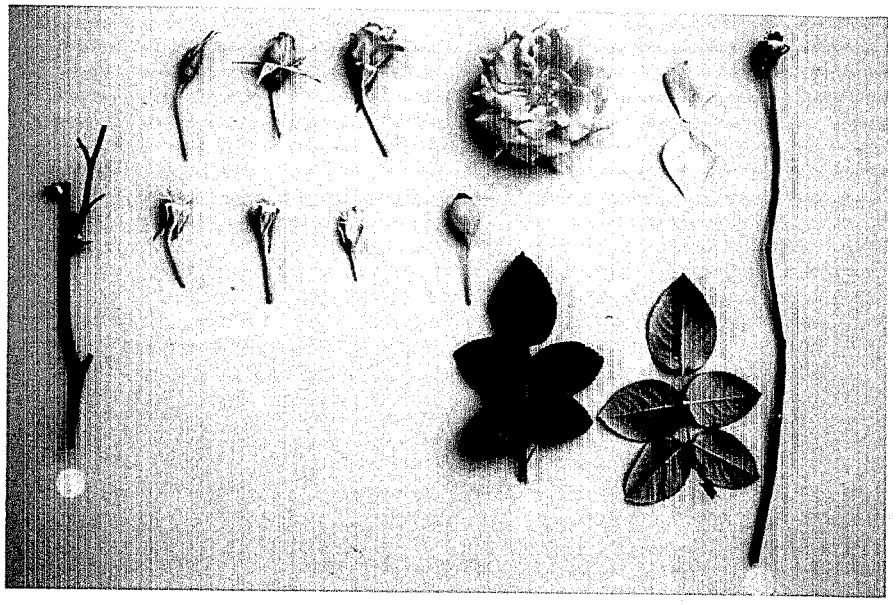
FIG. 1 depicts parts detached from the plant including, progressively, in the top row, flower stems (in side view) having, from left to right, an immature flower bud with sepals still up, a flower bud with sepals partly down, a flower in correct stage for cutting, a flower in full open stage showing stamens, two flower petals, bottom petal showing underside, and top petal showing upper side of petal. No. 6 shows a typical stem branching pattern. Middle row left to right depicts a flower stem and receptacle with petals removed, a flower stem and receptacle with flower petals and stamens removed, a flower stem and receptacle split in cross section, a rose hip, five-leaflet leaf top view, a five-leaflet leaf under side view, and a typical flower stem with foliage removed.
Figure 2:
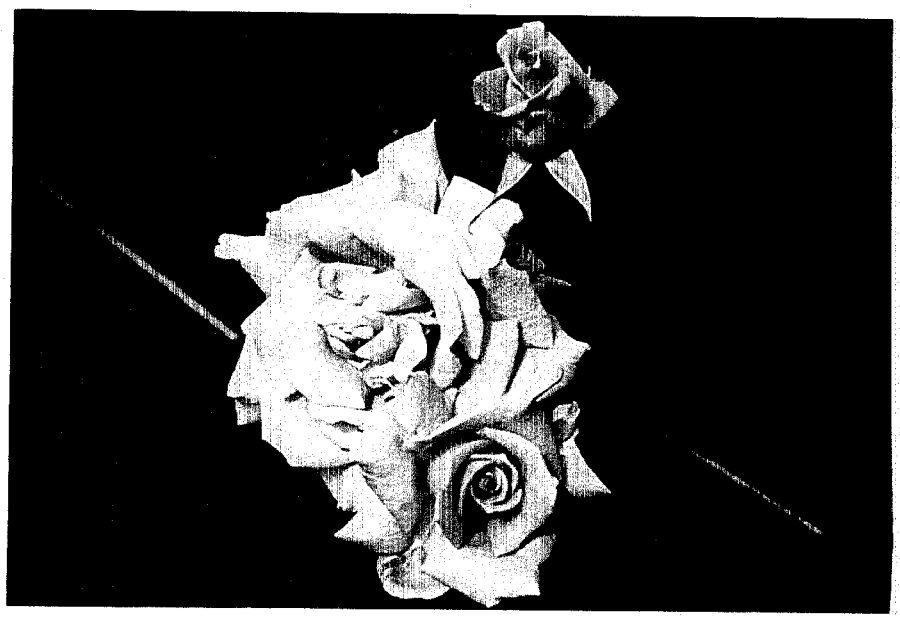
FIG. 2 shows the flowers in various stages from a tight bud to an open flower.

The following description was made during October 1994 of rose plants of the new and distinct variety growing in a greenhouse at Carlton, Oreg. Color designations are to *Royal Horticulture Society Colour Chart.*

Flower:

*Flowers borne.*—Sometimes singly, usually three to a stem on normal srength stems averaging 24" in length.

*Quantity of bloom.*—Abundant in greenhouse.

*Continuity.*—Continuous in greenhouse.

*Fragrance.*—Moderate.

*Bud.*—Sepals: permanent; recurved; of average length. Inside surface: Yellow-green Group 146D. Outside surface: Green Group 139C. Peduncle: medium length averaging 2"; medium weight; erect; almost smooth; few prickles; of a yellow-green color. Before calyx breaks: Size: medium. Form: medium pointed without foliaceous appendages on the surface of the bud. As calyx breaks: Color: Red-purple Group 70-C. As first petal opens: Size: medium. Form: medium pointed. Color: Outside: Red-purple Group 65-B. Inside: Red-purple Group 68-B. Opening: It opens up well.

*Bloom.*—Size when fully open: medium, 4" to 5". Petalage: double; from 24 to 30 petals; arranged regularly. Form: high centered at first; becoming open centered; petals at first loosely rolled outward, remaining loosely rolled outward at maturity.

*Petals.*—Medium soft; with inside satiny; outside satiny. Shape: Outer: Ovate with base flat. Intermediate: Ovate with round apex. Inner: Ovate with round apex. Color: Color of newly opened flowers in July 1995: Outer petal: Outside surface: Red-purple Group 69-B. Inside surface: Purple Group 77-D. Intermediate petal: Outside surface: Red-purple Group 69-B. Inside surface: Purple Group 77-D. Inner petal: Outside surface: Red-purple Group 69-B. Inside surface: Purple Group 77-D. Color of flower three days after opening in July 1995: Outer petal: Outside surface: Red-purple Fan 69-B. Inside surface: Purple Group Fan 77-D. Inner petal: Outside surface: Red-purple Group Fan 69-BC. Inside surface: Purple Group Fan 77-D.

*General color effect.*—Newly open flower: uniform color throughout flower. Flowers three days open: center of flower is a little darker as outside petals start to fade slightly.

*Behavior.*—Petals persist.

*Flower longevity.*—On bush in greenhouse eight days in July; cut flowers grown in greenhouse keep at living room temperature six days during July.

Reproductive organs:

*Stamens.*—Many; arranged irregularly. Filaments: many. Color: white. Anthers: all open at once; medium length. Color: yellow. Seldom an anther fused with a petaloid. Pollen: abundant; gold. Pistils: medium number. Styles: uneven; medium length; thin; loosely bunched. Stigma: white. Ovaries: all enclosed in receptacle. Hips: Ovoid with inconspicuous neck; very smooth; walls medium thick; reddish. Seeds: medium number; medium size.

Plant:

*Foliage.*—Leaves: compound comprised of five or seven leaflets; moderately abundant; medium size; leathery. Leaflets: ovate with apex obtuse, base round, margin simply serrate. Color: Mature upper surface: Green Group 139-A. Mature under surface: Green Group 139-B. Young upper surface: Green Group 137-A. Young under surface: Green Group 147-B. Rachis: heavy. Upper side: grooved. Under side: moderately thorny. Stipules: moderately long; medium width short points; turning out an angle of less than 45°. Disease: Resistance comparable to the average variety growing under the same cultural conditions.

*Growth.*—Habit: upright; average height of 4½ to 5 feet. Growth: modertely vigorous. Canes: moderately heavy. Main stems: dull. Color: Yellow-green Group 146-A. Prickles: few. Color: Yellow-green Group 152-D. Hairs: none. Branches: dull. Color: Yellow-green Group 146-B. Prickles: few. Color: Yellow-green Group 152-D. Hairs: none. New Shoots: dull. Color: Yellow-green Group 144-A. Prickles: few. Color: Yellow-green Group 152-D. Hairs: none.

I claim:

1. A new and distinct variety of rose plant of the Hybrid Tea class found as a seedling from an unnamed seed parent and a pollen parent entitled 'Blue Moon,' characterized by the purple color of its flowers, which is maintained as flower opens, and its ability to yield flowers on a continuous basis when grown in a greenhouse, substantially as shown and described.

* * * * *